(12) United States Patent
Lovett et al.

(10) Patent No.: US 6,641,541 B1
(45) Date of Patent: Nov. 4, 2003

(54) METHOD AND APPARATUS FOR A MORPHOLOGY-PRESERVING SMOOTHING FILTER

(75) Inventors: Eric G. Lovett, Roseville, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 214 days.

(21) Appl. No.: 09/626,361

(22) Filed: Jul. 27, 2000

(51) Int. Cl.$^7$ ................................. A61B 5/02
(52) U.S. Cl. ........................ 600/508; 327/551
(58) Field of Search .................... 600/508, 509, 600/520; 128/901; 607/9; 327/551, 552; 333/181

(56) References Cited

U.S. PATENT DOCUMENTS 5,904,708 A   5/1999  Goedeke ............... 607/18
5,941,830 A   8/1999  Williams .............. 600/509
5,944,744 A   8/1999  Paul et al. ............. 607/9
5,999,845 A * 12/1999 dePinto ................ 600/509

* cited by examiner

Primary Examiner—George R. Evanisko
Assistant Examiner—Roderick Bradford
(74) Attorney, Agent, or Firm—Schwegman, Lundberg, Woessner & Kluth, P.A.

(57) ABSTRACT

A method and apparatus for implementing a signal morphology preservation smoothing scheme. The smoothing scheme includes generating an output signal representative of a filtered version of the input signal, wherein the output signal is generated by adaptively removing low amplitude, high frequency noise components while simultaneously preserving signal morphology of the input signal. The smoothing scheme includes comparison of a distance metric against a distance threshold to determine whether an initial smoothed version of the input signal would be oversmoothed or undersmoothed. Then the smoothing scheme appropriately increments, decrements, or maintains the initial level of smoothing to generate an optimal smoothed signal representative of the output signal.

26 Claims, 5 Drawing Sheets

METHOD AND APPARATUS FOR A MORPHOLOGY-PRESERVING SMOOTHING FILTER

FIELD OF THE INVENTION

The present invention relates generally to signal processing. More particularly, the present invention relates to systems and methods for providing noise filtering while preserving signal morphology.

BACKGROUND OF THE INVENTION

To identify and/or monitor a state or event, such as a physiologic state or event, sensed signals or waveforms representative thereof are typically used. Once the relationship between the sensed signals or waveforms and the corresponding physiologic state or event is established, the signals can also be used to diagnose a condition and/or configure therapy delivery systems or methods.

For example, in the area of cardiac monitoring and/or therapy, implantable devices are employed for sensing cardiac signals, diagnosing conditions, and providing therapy. Such devices include electrodes for sensing and sense amplifiers for recording and/or deriving sensed event signals from electrical currents associated with cardiac activity, i.e., intracardiac or remote electrograms (EGMs). Implantable devices which also provide therapy include pacemakers, cardioverter/defibrillators, cardiomyostimulators, neurostimulators, and drug delivery devices. Such implantable devices are programmable and/or can be interrogated by an external programmer through the use of bi-directional radio frequency (RF) telemetry to exchange data and commands via uplink and downlink RF telemetry transmissions through the patient's skin.

Sensed signals detected by the implantable device and transmitted to and received by the external programmer comprise a continuous signal stream characterized by periodic repetition and impulse-like spikes in its waveform shape which correspond to electrical activations of the heart. Since these sensed signals represent a cardiac event or state, the spatial resolution or waveform morphology of a signal and its change over time are extremely valuable because conditions of the heart may be diagnosed and treatments configured based on such waveform morphology. Unfortunately, because the electrodes of implantable devices cannot be completely isolated from electrical currents associated with non-cardiac tissue, e.g., other muscles, and/or due to the sensed signals having to travel through tissue, such as the patient's skin, to be transmitted to the external programmer, it is not uncommon for sensed signals to be susceptible to noise and/or loss of spatial resolution.

With conventional signal processing, input signals are similarly filtered regardless of the actual morphology of the signals. Thus, there is a tendency for certain sections of waveforms to be oversmoothed, or over-filtered, and/or artificial distortions such as waveform discontinuities to be created. Hence, conventional signal processing can introduce artificial waveform morphology into a processed signal which can result in misdiagnosis or improper therapy.

Thus, there is a need for a signal processing scheme that can provide noise filtering while preserving signal morphology. There is a further need for a signal processing scheme that can provide real-time adaptive filtering, particularly of low amplitude, high frequency signal components from a continuous stream signal, while leaving high amplitude features of the signal intact at all frequencies.

SUMMARY OF THE INVENTION

The present invention provides a signal morphology preservation smoothing scheme. The smoothing scheme includes generating an output signal representative of a filtered version of an input signal, wherein the output signal is generated by adaptively removing low amplitude, high frequency noise components while simultaneously preserving morphology of the input signal.

One embodiment of the invention relates to a method for filtering an input signal detected by at least one detector. The method includes generating an output signal representative of a filtered version of the input signal by adaptively removing low amplitude, high frequency noise components from the input signal while simultaneously preserving morphology of the input signal.

Another embodiment of the invention relates to a system for filtering an input signal detected by at least one detector. The system includes a processor coupled to the detector and the processor configured to receive the input signal and generate an output signal representative of a filtered version of the input signal by adaptively removing low amplitude, high frequency noise components from the input signal while simultaneously preserving morphology of the input signal.

Another embodiment of the invention relates to a system for filtering an input signal detected by at least one detector. The system includes means for receiving the input signal. The system further includes means for generating an output signal representative of a filtered version of the input signal by adaptively removing low amplitude, high frequency noise components from the input signal while simultaneously preserving morphology of the input signal.

BRIEF DESCRIPTION OF THE DRAWINGS

The preferred embodiments of the invention will become more fully understood from the following detailed description, taken in conjunction with the accompanying drawings, wherein like reference numerals denote like elements, and in which.

DETAILED DESCRIPTION OF THE INVENTION

The following description is preferably directed to filtering of cardiac signals. Alternatively, the other embodiments of the present invention can be applied to a variety of biological signals such as neural spike trains. It is also contemplated that the preferred embodiments of the present invention can be applied to a variety of non-biological signals such as signals produced by a digital communications system.

Figure 1:
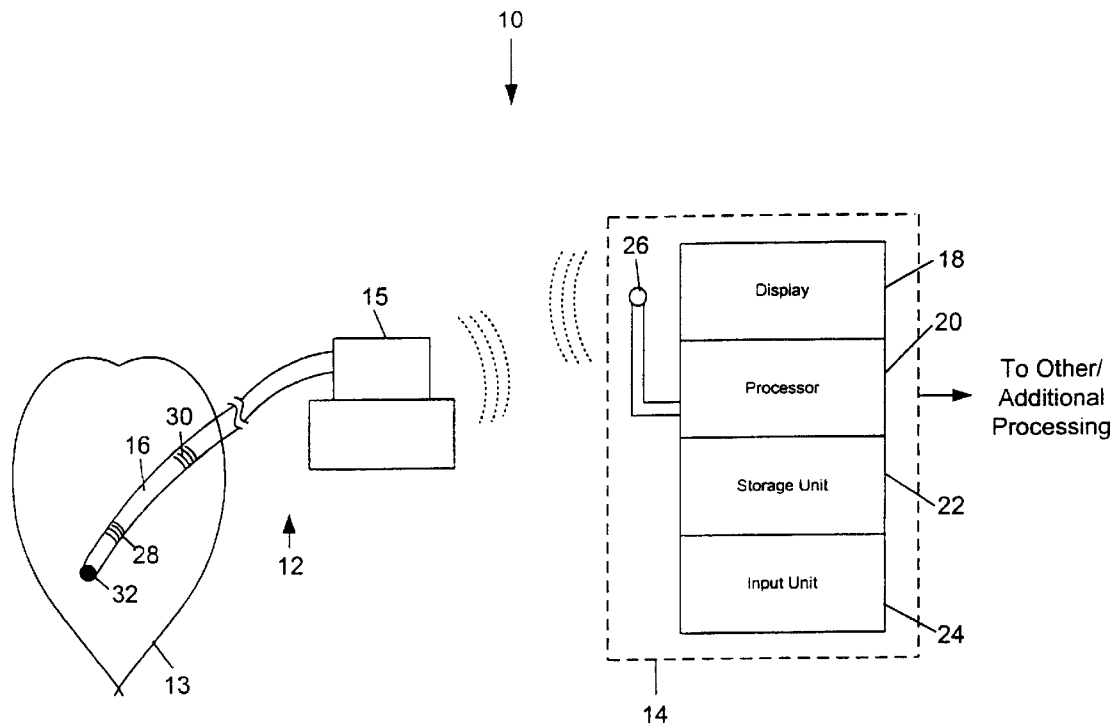
FIG. 1 is a block diagram of an implantable medical device system which employs an embodiment of the present invention.

Referring to FIG. 1, there is shown the major components of an implantable medical device system 10. System 10 includes an implantable medical device 12 and an external monitor or programmer 14. Device 12 may, for example, be an implantable cardiac device which is implanted in a patient proximate his or her heart 13 and includes a housing 15 and at least one cardiac lead 16. Programmer 14 includes a display 18, a processor 20, a storage unit 22, an input unit 24, and an antenna 26. System 10 is configured to sense cardiac signals from the patient's heart using device 12, communicate sensed cardiac signals from device 12 to programmer 14, and communicate command signals from programmer 14 to device 12 to control a program device 12.

In one exemplary embodiment, system 10 may be configured to be an implantable cardiac defibrillation system. In this embodiment, the at least one cardiac lead 16 is a ventricular lead and includes at least three electrodes—a first electrode 28, a second electrode 30, and a pacing electrode 32. Device 12 includes electronic circuitry which is coupled to the electrodes 28, 30, 32 in cardiac lead 16.

First electrode 28 is located between electrodes 30, 32 along a peripheral surface of cardiac lead 16. First electrode 28 may be a defibrillation coil electrode electrically coupled to the electronic circuitry in housing 15 through a lead conductor housed and electrically insulated within the body of cardiac lead 16. Second electrode 30 is similar to and positioned proximal to first electrode 28 along cardiac lead 16 such that cardiac lead 16 can be implanted within the vasculature with first electrode 28 positioned at the right ventricle and second electrode 30 positioned at either the right atrial chamber or a major vein leading to the right atrial chamber. In this manner, cardiac signals from the heart (e.g., cardiac morphology signals such as intracardiac electrograms (EGMs)) can be sensed, or detected, via first and second electrodes 28, 30. Alternatively, an electrically conductive portion of housing 15 may be used in conjunction with first and second electrodes 28, 30 to allow cardiac signals to be sensed between three electrodes or sensor locations.

Pacing electrode 32 is located at or adjacent to a distal end of cardiac lead 16. Pacing electrode 32 further permits rate signals to be provided to the ventricular region of the heart. For example, rate signals can be provided between pacing electrode 32 and first electrode 28, and cardiac signals can be sensed between first and second electrodes 28, 30. In general, each electrode may be used for sensing signals from and/or applying signals to the heart.

Cardiac and/or rate signals from electrodes 28–32 are received and processed in device 12. Cardiac signals may be digitized and stored in device 12. Device 12 may also be utilized to analyze the cardiac signals for automatic therapy delivery (programmed instructions) and/or to transmit the cardiac signals to an external programmer for analysis. Command signals for controlling the operation of device 12 can also be sent between programmer 14 and device 12. Communication between device 12 and programmer 14 can be accomplished by radio frequency (RF) telemetry as is well-known in the art, via transceivers included in each of device 12 and programmer 14.

Programmer 14 includes a backplane for coupling display 18, processor 20, storage unit 22, input unit 24, and antenna 26 to each other. Preferably, each of display 18, storage unit 22, input unit 24, and antenna 26 couples to processor 20. Input unit 24 can include one or more of, but is not limited to, a mouse, a joystick, a keyboard, a trackball, a touch screen, a light wand, and a voice control.

Signals transmitted by implantable device 12 are received by antenna 26 and are communicated to processor 20 for signal processing. Processor 20 can be a microprocessor, as is well-known in the art, and performs, among others, analog-to-digital conversion, signal amplification, signal calibration, signal reconstruction, and other operations such that the signals may be graphically displayed on display 18 or otherwise be in a suitable state for transmitting to other devices. Alternatively, other processors (not shown) may be used to perform the signal processing and the processed signals then returned to programmer 14.

It is also contemplated that device 12 may function autonomously of programmer 14. Device 12 may sense cardiac signals from the patient's heart, perform the filtering scheme to be described below, and utilize the filtered signals for detection and decision-making processes.

Although cardiac signals received from device 12 are less susceptible to noise, loss of spatial resolution, and/or missensing due to myopotentials than, for example, surface electrocardiograms (EKGs), intracardiac electrograms can be corrupted by myopotentials, electromagnetic interference, intermittent lead connections, and other nuisance factors that degrade signal quality and can impair rhythm diagnosis, thereby resulting in improper therapy decisions. Hence, processor 20 is further configured to implement a signal morphology preservation smoothing scheme to the received cardiac signals. Alternatively, the signal morphology preservation smoothing scheme may be implemented in other processors or computing systems coupled to or in communication with programmer 14. Alternatively, the signal morphology preservation smoothing scheme may be implemented in a processor within the implantable device.

It should be understood that systems other than system 10 may be utilized to generate input signals for the signal morphology preservation smoothing scheme of the present invention. For example, system 10 may generate surface EKG signals as the input signals for the smoothing scheme. In another example, other biological signals such as neural spike trains may be the input signals. In still another example, system 10 may produce signals that have originated from non-biological sources such as digital communication systems. Thus, any one of a variety of signals that is characterized by a continuous stream or train, has impulse-like spikes, and where it is of interest to adaptively preserve signal morphology while removing noise can benefit from the smoothing scheme of the present invention.

Figure 2:
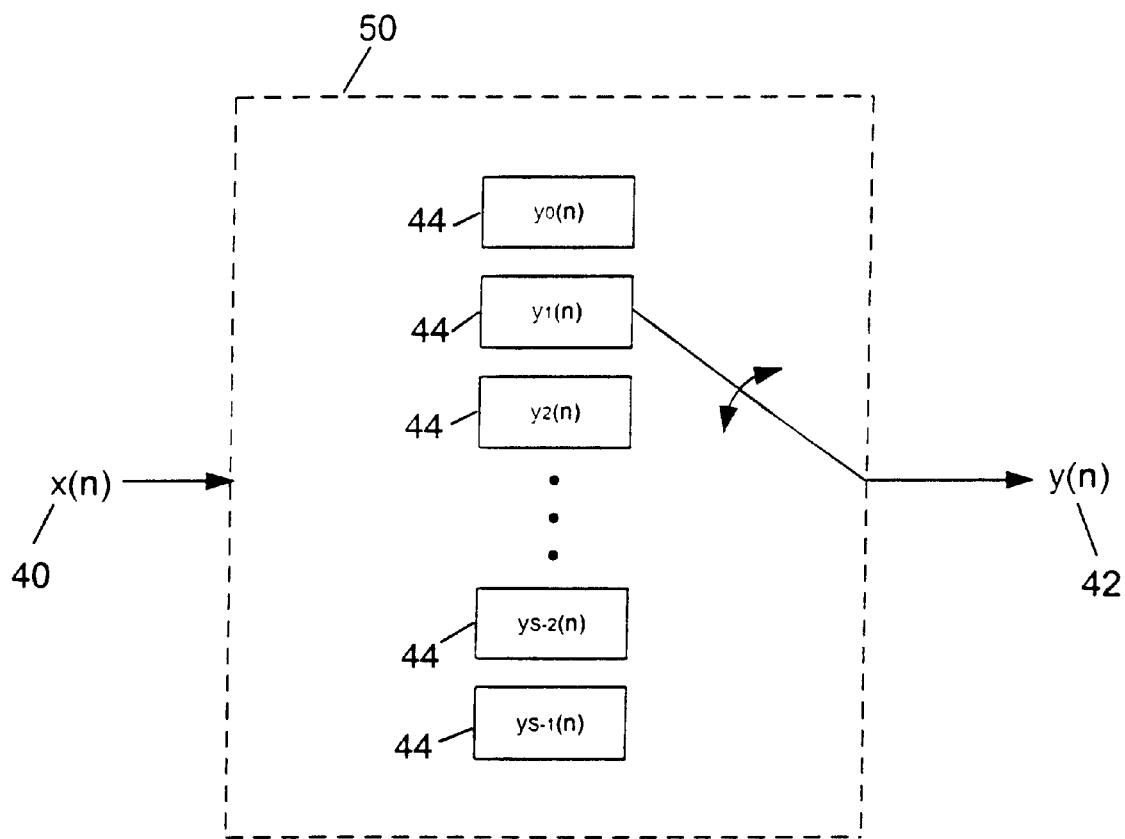
FIG. 2 is a block diagram of a filtering processor which implements a signal morphology preservation smoothing scheme of the present invention.
Figure 3:
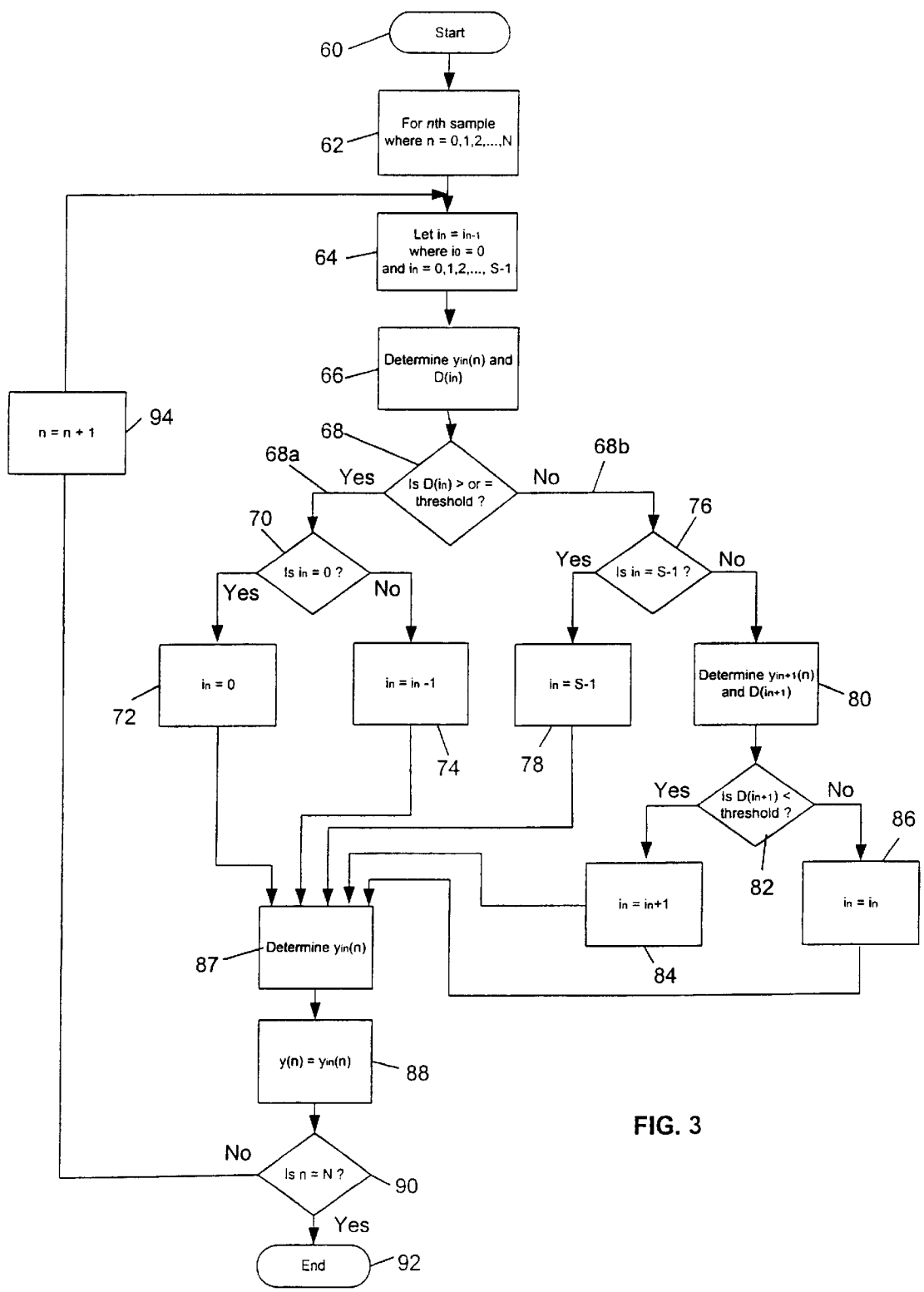
FIG. 3 is a flowchart of a signal morphology preservation smoothing scheme implemented in the implantable medical device system of FIG. 1 or the filtering processor of FIG. 2.

Referring to FIGS. 2 and 3, cardiac signals, or more generally an analog data stream, are sampled at discrete times to convert the signals into digital signals or a digital data stream. The sampling rate, for example, can be on the order of 200 samples per second, although other sampling rates may also be used. These digitized signals, hereinafter referred to as input signals $x(n)$ 40 (where n is the sampling index and $n=0, 1, 2, \ldots, N$), are the inputs to the smoothing scheme. The smoothing scheme is implemented in a filtering processor 50. Filtering processor 50 is included in programmer 14, processor 20, or in other systems comprised of hardware, firmware and/or software capable of implementing the smoothing scheme including the implantable device. The outputs of the smoothing scheme are output signals $y(n)$ 42, wherein each nth output signal 42 is the corresponding output to the nth input signal 40. Each of output signals $y(n)$ 42 is an appropriately corrected or "smoothed" version of its corresponding input signals $x(n)$ 40. These smoothed versions are referred to as smoothed signals $y_{i_n}(n)$ 44, where $i_n$ is a smoothing index for each nth sample and $i_n=0, 1, 2, \ldots, S-1$ (where S is the total number of smoothed versions to select from for the nth sample).

After the cardiac signals have been transformed into input signals x(n) 40, each nth sample of input signals x(n) 40 can be adaptively corrected or smoothed in quasi-real-time or in real-time. Referring to FIG. 3, there is shown a flowchart of one embodiment of the signal morphology preservation smoothing scheme. The smoothing scheme includes a start step 60, a nth sample specification step 62, a smoothing index initialization step 64, a determine initial smoothed signal and distance metric step 66, an oversmoothing inquiry step 68, an oversmoothing branch 68a, an undersmoothing branch 68b, a lower limit smoothing index check step 70, a lower limit smoothing level step 72, a decrement smoothing level step 74, an upper limit smoothing index check step 76, an upper limit smoothing level step 78, a determine next smoothed signal and distance metric step 80, an undersmoothing inquiry step 82, an increment smoothing level step 84, a maintain smoothing level step 86, a determine appropriate smoothed signal step 87, an output signal step 88, an end of data samples check step 90, an end step 92, and an incrementor step 94.

The smoothing scheme is initiated by steps 60–62 and steps 64–94 are invoked a total of N+1 times to generate N+1 output signals y(n) 42 respectively corresponding to N+1 input signals x(n) 40.

In step 64, smoothing index $i_n$ for the nth sample is initially set to the smoothing index previously determined for the (n−1)th sample (i.e., $i_n = i_n - 1$). For the first sample (i.e., n=0), the smoothing scheme provides a default initial smoothing index of $i_0 = 0$ (if maximum fidelity is initially desired). Alternatively, the default initial smoothing index for n=0 may be $i_0 = S-1$ (if maximum noise immunity is initially desired). In still another alternative, the default initial smoothing index for n=0 may be any level of smoothing (i.e., $i_0$ is any integer between and including 0 and S−1).

The initial smoothing index $i_n$ for the nth sample is set to the smoothing index for the (n−1)th sample because there is a fairly high probability that the nth and (n−1)th samples of input signals x(n) 40 are similar such that both samples would require a similar amount of smoothing. Moreover, using the smoothing index from the previous sample as the starting point reduces unnecessary iterations and computations in determining an appropriate smoothing index $i_n$.

In one embodiment, the total number of possible smoothed signals $y_{in}(n)$ 44 to select from is five (i.e., S−1=4). Alternatively, the number of possible smoothed signals may be more or less than five, such as being S−1=3, 4, or 7. Whatever the value of S−1, for each nth sample, the amount or degree of smoothness increases as the value of sampling index $i_n$ increases. In other words, $y_o(n)$ is representative of the least smoothed version of x(n) and $y_{S-1}(n)$ is representative of the most smoothed version of x(n).

After step 64, smoothed signal $y_{in}(n)$ and a distance metric $D(i_n)$ corresponding to the initial smoothing index $i_n$ are determined in step 66. In one embodiment, when S−1=4, the equations for smoothed signals $y_{in}(n)$ 44 can be:

$$y_o(n) = x(n) \quad (1a)$$

$$y_1(n) = \frac{1}{2} \sum_{m=-1}^{0} x(n+m) \quad (1b)$$

$$y_2(n) = \frac{1}{4} \sum_{m=-2}^{1} x(n+m) \quad (1c)$$

$$y_3(n) = \frac{1}{8} \sum_{m=-4}^{3} x(n+m) \quad (1d)$$

$$y_4(n) = \frac{1}{16} \sum_{m=-8}^{7} x(n+m). \quad (1e)$$

As shown in Equation 1a, the least smoothed signal $y_o(n)$ is its corresponding input signal x(n). In order to use input signals from samples greater than the nth sample (i.e., Equations 1c–1e) while implementing the scheme in real-time or quasi-real-time, the scheme outputs output signals 42 with a slight time delay such that there will be enough time for processor 50 to receive the necessary (n+1)th, (n+2)th, etc. samples prior to the determination of the output signal y(n) for the nth sample. For example, the time delay can be on the order of one millisecond. In step 66, using the value of smoothing index $i_n$ from step 64, one smoothed signal (i.e., the initial nth sample smoothed signal) is calculated using the appropriate one of Equations 1a–1e.

Alternatively, smoothed signals $y_{in}(n)$ 44 may be defined by equations other than Equations 1a–1e above. For example, equations for smoothed signals $y_{in}(n)$ may comprise finite impulse response (FIR), infinite impulse response (IIR), or other filters, including nonlinear filters, with outputs temporally aligned at n. Generally, equations defining smoothed signals $y_{in}(n)$ 44 are characterized by an increasing deviation from its corresponding input signal x(n), i.e., decreasing high-frequency content, as the value of smoothing index $i_n$ increases. At the same time, as the value of smoothing index $i_n$ increases, the amount of low amplitude, high frequency noise in x(n) decreases.

Distance metric $D(i_n)$ calculates the amount of deviation or difference between, at least, the calculated initial nth sample smoothed signal and its corresponding nth sample input signal x(n). In one embodiment, distance metric $D(i_n)$ is given by:

$$D(i_n) = |y_{in}(n) - x(n)| \quad (2)$$

In another embodiment, distance metric $D(i_n)$ may be given by:

$$D(i_n) = \frac{1}{4} \sum_{m=n-2}^{n+1} |y_{in}(m) - x(m)|. \quad (3)$$

Thus, depending on the characteristics of input signals x(n) 40, the type of smoothing or correction desired, and/or the particular application of output signals y(n) 42, the number and types of equations for the smoothed signals as well as appropriate distance metrics can be chosen.

Once the nth sample initial smoothed signal and its corresponding distance metric have been calculated in step 66, step 68 checks to see whether the amount of smoothness initially/currently chosen (i.e., the initial smoothed signal) exceeds a desired amount of smoothing, i.e., a distance threshold $\epsilon$. Distance threshold $\epsilon$ is preferably predetermined and stored in processor 50 to be invoked for each nth sample. Distance threshold $\epsilon$ is selected based on the desired balance between the amount of low amplitude, high frequency noise removal desired and the amount of signal morphology preservation desired. By careful selection of distance threshold $\epsilon$, the scheme is capable of selecting a minimal level of smoothing when input signal x(n) contains sharpest, high amplitude features, and a maximum level of smoothing when input signal x(n) contains low amplitude, high frequency noise features.

For example, for EKG signals (i.e., input signals x(n)) which occupy 60–70% peak-to-peak of a 8-bit dynamic range (i.e., range of −128 to +127), a value of $\epsilon$=3, 4, or 5 can be used. In another example, distance threshold $\epsilon$ can be automatically adaptive (i.e., constantly calibrating) while the smoothing scheme is in progress. Such a feature may be advantageous when the peak-to-peak amplitudes of the input signals change from one sustainable period of time to another. This would prevent "false" oversmoothing or undersmoothing from occurring from the use of a non-calibrating distance threshold.

Step 68 determines whether distance metric $D(i_n)$ (from step 66) is greater than or equal to distance threshold $\epsilon$. If $D(i_n)$ is $\geq \epsilon$ (i.e., the initial/current smoothing level would be too much smoothing), then the final smoothing level for the nth sample will be the next lower level of smoothing (i.e., final $i_n=i_n-1$) (see oversmoothing branch 68a). Otherwise when $D(i_n)$ is $<\epsilon$ (i.e., the initial/current smoothing level may not be enough smoothing), the scheme will check to see if the next higher level of smoothing would also be within $\epsilon$. If yes, then the final smoothing level for the nth sample will be the next higher level of smoothing (i.e., final $i_n=i_n+1$) (see undersmoothing branch 68b). In this manner, the scheme maintains adaptability between fidelity to relatively high amplitude features and smoothing of low amplitude noise.

At oversmoothing branch 68a, step 70 checks for the lower limiting case of smoothing index $i_n$ (i.e., $i_n=0$). If smoothing index $i_n$ initially specified in step 64 is already at zero, then step 72 directs the final smoothing index $i_n$ for the nth sample to remain at $i_n=0$. Otherwise, if the initial smoothing index is greater than zero, then step 74 directs the initial smoothing index $i_n$ for the nth sample to switch to the next lower level of smoothing (i.e., final $i_n=i_n-1$).

At undersmoothing branch 68b, step 76 checks for the upper limiting case of smoothing index $i_n$ (i.e., $i_n=S-1$). If smoothing index $i_n$ initially specified in step 64 is S−1, then step 78 directs the final smoothing index $i_n$ for the nth sample to remain at $i_n=S-1$. Otherwise, if the initial smoothing index is less than S−1, then step 80 calculates the smoothed signal and distance metric for the next higher level of smoothing (i.e., at $i_n+1$). If the distance metric at in+1 in step 80 is also less than distance threshold $\epsilon$ (i.e., $D(i_n+1)<\epsilon$), then step 84 directs the initial smoothing index $i_n$ for the nth sample to switch to the next higher level of smoothing (i.e., final $i_n=i_n+1$). As long as $D(i_n+1)<\epsilon$, the $(i_n+1)$th smoothing level is a better correction of its corresponding input signal x(n) than the $i_n$th smoothing level. Otherwise, if the calculated distance metric of ($i_n+1$) in step 80 is not less than distance threshold $\epsilon$ (i.e., $D(i_n+1) \geq \epsilon$), then step 86 directs the initial smoothing index $i_n$ for the nth sample to remain as is (i.e., $i_n=i_n$) since switching to the next higher of smoothing would be too much smoothing or, in other words, exceed the desired tolerance amount of deviation from the nth sample input signal.

Notice that in this embodiment, there can be at most one transition or change in the smoothing level for any pair of successive neighboring samples. This prevents artificial jumps or discontinuities from being created in output signals y(n), since although corrected as discrete samples, y(n) is typically viewed as a continuous stream of data. Moreover, at a sufficiently high sampling rate, there should be minimal gross change in the input signals from the nth to the (n+1)th sample. Thus, the optimal smoothing level would be fairly constant for each pair of successive samples, and calculating all S−1 smoothed signals and its corresponding distance metrics and checking to see whether or not these distance metrics exceed the distance threshold for each nth sample would be unnecessary.

However, it should be understood that the smoothing scheme can be tailored to the particular application to provide, for example, multiple iterations of incrementing and/or decrementing the smoothing level in each nth sample. In such a case, the distance metrics that are less than the distance threshold may be compared against each other to determine which smoothing level is most desirable. And as such, there could be more than one smoothing level transition between a sample to its nearest neighboring sample.

Once the final smoothing index $i_n$ for the nth sample has been decided by one of steps 72, 74, 78, 84, and 86, this final smoothing index is used to determine the final or optimal smoothed signal for the nth sample (i.e., $y_{in}(n)$) using one of Equations 1a–1e in step 87. In one embodiment, the final smoothed signal would only need to be calculated if the final smoothing index came from step 74 (i.e., $i_n=i_n-1$) since in all other cases, the final smoothed signal would already have been determined in step 66 or 80.

Then in step 88, the output signal y(n) is set to be the final smoothed signal $y_{in}(n)$ from step 87 (i.e., $y(n)=y_{in}(n)$). If all the samples have been corrected (i.e., n=N), then step 90 directs the smoothing scheme to end with step 92. Otherwise, step 90 directs the smoothing to be performed for the next sample (i.e., n=n+1 in step 94).

Figure 4:
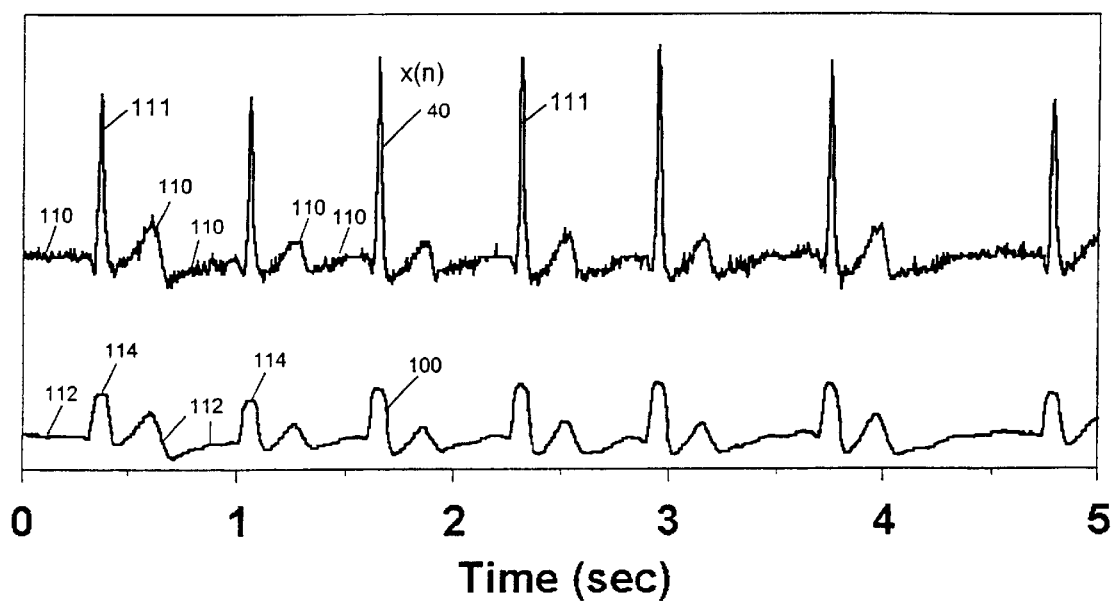
FIG. 4 is a sample waveform diagram representative of an input signal x(n) and a corresponding output signal using a conventional filtering scheme.
Figure 5:
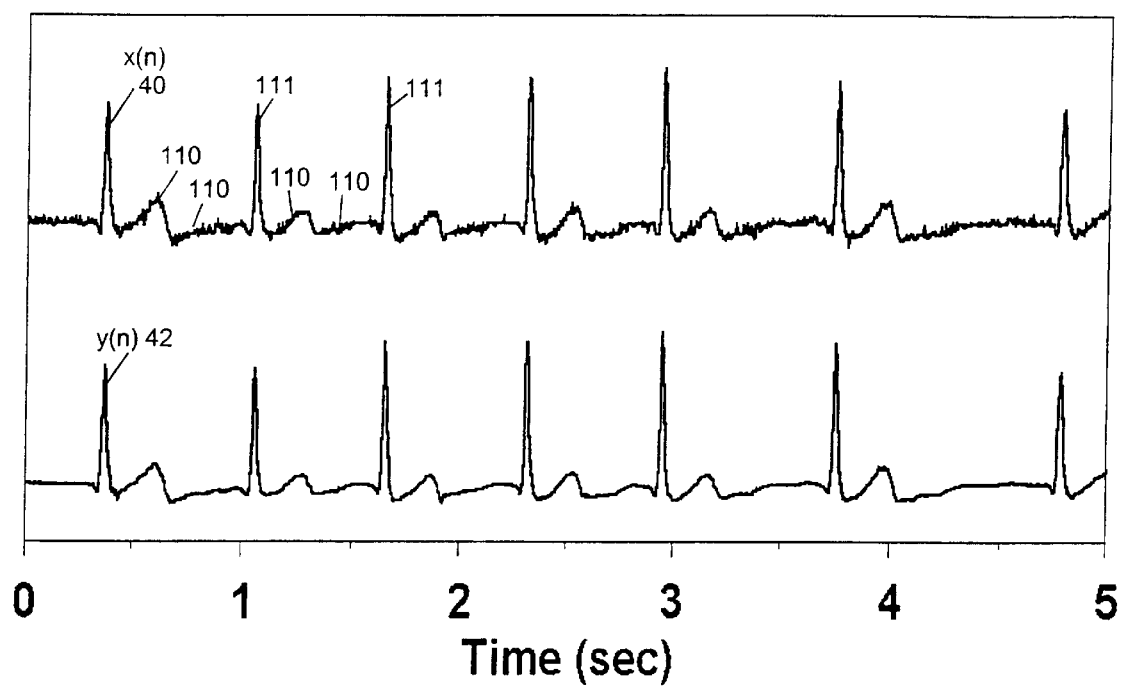
FIG. 5 is a sample waveform diagram representative of an input signal x(n) and its corresponding output signals y(n) using the signal morphology preservation smoothing scheme of FIG. 3.

In FIGS. 4–5, an illustrative comparison of output signals generated using a conventional filter and output signals generated using an embodiment of the smoothing scheme is provided. FIG. 4 shows the input signal x(n) 40 on top and the corresponding output signal 100 generated using a conventional filter on the bottom. FIG. 5 shows input signal x(n) 40 on top and the corresponding output signals y(n) 42 generated using the smoothed scheme on the bottom.

In FIG. 4, input signals x(n) 40 includes sections containing low amplitude, high frequency noise 110 and sharp peaks 111. Notice that in output signal 100, the low amplitude, high frequency noise 110 in signal 40 has been effectively removed while still maintaining the waveform shape in those sections (see sections 112). However, significant information relating to sharp peaks 111 in signal 40 has been lost using the conventional filter (see sections 114). Sections 114 show that the conventional filter does a poor job of removing low amplitude, high frequency noise and simultaneously preserving waveform shape at all frequencies, particularly high amplitude features.

In contrast, output signal y(n) 42 in FIG. 5 reflects input signal x(n) 40 much more closely using the smoothing scheme. Output signal y(n) 42 shows effective removal of low amplitude, high frequency noise 110 while simultaneously preserving the waveform shape at all amplitudes and frequencies, such as sharp peaks 111. Thus, the smoothing scheme of the present invention provides adaptive filtering of input signals by balancing removal of undesirable signal components while simultaneously preserving waveform shape. The smoothing scheme provides real-time or quasi-real-time capability without sacrificing high fidelity or requiring a large number of computations. In this manner, the smoothing scheme can be used to facilitate identification and/or monitoring morphology devices or methods by functioning, for example, as a preprocessing stage for morphology-dependent schemes.

While the embodiments and applications of the invention illustrated in the figures and described above are presently preferred, it should be understood that these embodiments are offered by way of example only. For example, it is contemplated that the invention may be applied to input signals which remain in analog format. Accordingly, the present invention is not limited to a particular embodiment, but extends to various modifications that nevertheless fall within the scope of the appended claims.

What is claimed is:

1. A method for filtering an input signal, comprising:
generating an output signal representative of a filtered version of the input signal by adaptively removing noise components from the input signal, wherein each of the input signal and the output signal includes discrete samples; and
determining a desired filtering level from a number of filtering levels for each of the discrete samples of the input signal, wherein determining a desired filtering level includes determining an initial distance metric corresponding to an initial filtering level for each of the discrete samples of the input signal.

2. The method of claim 1, wherein the initial filtering level is a desired filtering level for an immediately preceding sample.

3. The method of claim 1, further comprising identifying a distance threshold representing a desired amount of signal smoothing, wherein determining a desired filtering level includes comparing the initial distance metric against the distance threshold.

4. The method of claim 3, further comprising selecting the distance threshold based on the input signal that balances removal of noise components with preserving a morphological representation of the input signal.

5. The method of claim 3, further comprising decreasing the initial filtering level by at least one filtering level to become the desired filtering level when the initial distance metric is at least equal to the distance threshold.

6. The method of claim 3, wherein determining a desired filtering level includes determining another distance metric corresponding to the initial filtering level incremented by one filtering level.

7. The method of claim 6, wherein at least one of determining an initial distance metric and determining another distance metric includes calculating a distance metric using $D(i_n)=|y_{in}(n)-x(n)|$, where $i_n$ represents a smoothing index, $D(i_n)$ represents a distance metric, $y_{in}(n)$ represents an nth sample smoothed signal, and $x(n)$ represents an nth sample input signal.

8. The method of claim 6, wherein at least one of determining an initial distance metric and determining another distance metric includes calculating a distance metric using $$D(i_n) = \frac{1}{4}\sum_{m=n-2}^{n+1} |y_{in}(m) - x(m)|,$$

where $i_n$ represents a smoothing index, $D(i_n)$ represents a distance metric, $y_{in}$ represents a sample smoothed signal, and x represents a sample input signal.

9. The method of claim 6, further comprising increasing the initial filtering level by at least one filtering level to become the desired filtering level when the another distance metric is smaller than the distance threshold.

10. A system, comprising a processor to receive an input signal and generate an output signal representative of a filtered version of the input signal by adaptively removing noise components from the input signal, wherein:
the input signal includes a number of discrete samples;
the processor is configured to determine a desired filtering level for each of the discrete samples of the input signal; and
the processor is configured to determine an initial distance metric corresponding to an initial filtering level to determine the desired filtering level.

11. The system of claim 10, further comprising a distance threshold that represents a desired amount of signal smoothing, wherein the processor is configured to compare the initial distance metric against the distance threshold.

12. The system of claim 11, wherein the processor is configured to select the distance threshold based on the input signal that balances removal of noise components with preserving a morphological representation of the input signal.

13. The system of claim 11, wherein the processor is configured to decrease by at least one filtering level the initial filtering level to set the desired filtering level when the initial distance metric is at least equal to the distance threshold.

14. The system of claim 11, wherein the processor is configured to determine another distance metric corresponding to the initial filtering level incremented by one filtering level.

15. The system of claim 14, wherein at least one of the initial distance metric and the another distance metric is determined using $D(i_n)=|y_{in}(n)-x(n)|D(i_n)=|y_{in}(n)-x(n)|$, where $i_n$ represents a smoothing index, $D(i_n)$ represents a distance metric, $y_{in}(n)$ represents an nth sample smoothed signal, and $x(n)$ represents an nth sample input signal.

16. The system of claim 14, wherein at least one of the initial distance metric and the another distance metric is determined using $$D(i_n) = \frac{1}{4}\sum_{m=n-2}^{n+1} |y_{in}(m) - x(m)|,$$

where $i_n$ represents a smoothing index, $D(i_n)$ represents a distance metric, $y_{in}$ represents a sample smoothed signal, and x represents a sample input signal.

17. The system of claim 14, wherein the processor is configured to increase by at least one filtering level the initial filtering level to set the desired filtering level when the another distance metric is smaller than the distance threshold.

18. A system for filtering an input signal, comprising:
means for receiving the input signal;
means for generating an output signal representative of a filtered version of the input signal by adaptively removing noise components from the input signal; and
means for determining a desired filtering level from a number of filtering levels for each discrete sample of the input signal,
wherein the input signal includes a number of discrete samples, and the means for determining includes means for calculating an initial distance metric corresponding to an initial filtering level for each of the discrete samples of the input signal.

19. The system of claim 18, wherein the initial filtering level is a desired filtering level for an immediately preceding sample.

20. The system of claim 18, further comprising a distance threshold representing a desired amount of signal smoothing, wherein the means for determining includes means for comparing the initial distance metric against the distance threshold.

21. The system of claim 20, wherein the processor is adapted to select the distance threshold based on the input signal that balances removal of noise components with preserving a morphological representation of the input signal.

22. The system of claim 20, wherein the means for determining includes means for decrementing the initial filtering level by at least one filtering level to become the desired filtering level when the initial distance metric is at least equal to the distance threshold.

23. The system of claim 20, wherein the means for determining includes means for calculating another distance metric corresponding to the initial filtering level incremented by one filtering level.

24. The system of claim 23, wherein at least one of the initial distance metric and the another distance metric is determined using $D(i_n)=|y_{in}(n)-x(n)|D(i_n)=|y_{in}(n)-x(n)|D(i_n)=|y_{in}(n)-x(n)|$, where $i_n$ represents a smoothing index, $D(i_n)$ represents a distance metric, $y_{in}(n)$ represents an nth sample smoothed signal, and $x(n)$ represents an nth sample input signal.

25. The system of claim 23, wherein at least one of the initial distance metric and the another distance metric is determined using $$D(i_n) = \frac{1}{4} \sum_{m=n-2}^{n+1} |y_{in}(m) - x(m)|,$$

where $i_n$ represents a smoothing index, $D(i_n)$ represents a distance metric, $y_{in}$ represents a sample smoothed signal, and x represents a sample input signal.

26. The system of claim 23, wherein the means for determining includes means for incrementing the initial filtering level by at least one filtering level to become the desired filtering level when the another distance metric is smaller than the distance threshold.

* * * * *